US006416774B1

(12) United States Patent
Radin et al.

(10) Patent No.: US 6,416,774 B1
(45) Date of Patent: *Jul. 9, 2002

(54) HOLLOW BONE MINERAL-LIKE CALCIUM PHOSPHATE PARTICLES

(75) Inventors: Shulamith Radin, Voorhees, NJ (US); Paul Ducheyne, Rosemont, PA (US); Sylvie Falaize, Lyons (FR); Portonovo S. Ayyaswamy, Broomall, PA (US)

(73) Assignee: The Trustees of the University of Pennsyvania, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/647,171

(22) Filed: May 9, 1996

(51) Int. Cl.⁷ .............................................. A01N 25/26
(52) U.S. Cl. ..................... 424/408; 424/409; 424/421; 424/423; 424/602; 424/403; 424/404; 424/406; 523/218; 523/219; 106/690
(58) Field of Search .................. 523/218, 219; 428/404, 403, 406; 427/213.31, 215; 264/4.3, 4.4, 4.6; 106/690; 424/408, 409, 421, 423, 426, 451, 602, 724, 489; 514/8

(56) References Cited

U.S. PATENT DOCUMENTS

| 3,960,583 A | | 6/1976 | Netting et al. .............. 106/122 |
|---|---|---|---|
| 4,293,540 A | * | 10/1981 | Shibita et al. ................. 424/26 |
| 4,340,642 A | * | 7/1982 | Netting et al. .............. 428/402 |
| 4,411,847 A | | 10/1983 | Netting et al. ................. 264/7 |
| 4,657,810 A | * | 4/1987 | Doyden .................... 428/313.9 |
| 4,842,863 A | * | 6/1989 | Nishimura et al. ......... 424/438 |
| 5,002,890 A | | 3/1991 | Morrison .................... 435/286 |
| 5,024,826 A | | 6/1991 | Linton ........................ 423/335 |
| 5,055,307 A | * | 10/1991 | Tjuru et al. ................. 424/493 |
| 5,204,106 A | | 4/1993 | Schepers et al. ............ 424/423 |
| 5,328,955 A | | 7/1994 | Rhee et al. ................. 525/54.1 |
| 5,356,617 A | * | 10/1994 | Shlossman .................... 424/63 |
| 5,480,844 A | | 1/1996 | Matsui et al. .................. 501/3 |
| 5,591,453 A | * | 1/1997 | Ducheyne et al. .......... 424/484 |
| 5,593,680 A | * | 1/1997 | Bara et al. .................. 424/401 |

FOREIGN PATENT DOCUMENTS

WO    WO 00/44681    8/2000

OTHER PUBLICATIONS

Radin, S., et al., "Transformation of bioactive glass granules into CA–P shells in vitro," *Bioceramics*, Proceedings of the 10th International Symposium on Ceramics in Medicine, Paris, France, Oct. 1997, 10, 45–48, XP–000978406.

(List continued on next page.)

*Primary Examiner*—Neil S. Levy
(74) *Attorney, Agent, or Firm*—Woodcock Washburn LLP (57) ABSTRACT

Hollow particles having a shell substantially composed of calcium-phosphate, methods for preparing the same, and methods of use are disclosed. The particles are obtained by differential immersion of silica-based, calcium and phosphate containing glass particles.

7 Claims, 4 Drawing Sheets

OTHER PUBLICATIONS

Supplementary European Search Report dated Jan. 22, 2001.

Ayyaswamy et al. (Invests.), Executive Summary and Research Project Description of invention, Sep. 1995, 27 pages.

Ducheyne, P., "Bioglass Coatings and Bioglass Composites as Implant Materials", *J. Biomed. Mat. Res.*, 1985, 19, 273–291.

Ducheyne, P., "The Use of Bioactive Glass Particles as Microcarriers in Microgravity Evironment", *Microgravity Science & Applications*: Program Tasks and Bibliography for FY 1995, NASA Technical Memorandum 4735, 1996.

Heinoken et al., "A New and Convenient Colorimetric Determination of Inorganic Orthophosphate and its Application to the Assay of Inorganic Pyrophosphate", *Anal. Biochem.*, 1981, 113, 313–317.

O'Connor et al., "The Kinetics for the Solution of Silica in Aqueous Solutions", *J. Phys. Chem.*, 1958, 62, 1195–1198.

Schepers et al., "Bioactive Glass Particles of Narrow Size Range: A new Material for the Repair of Bone Defects", *Implant Dentistry*, 1993, 2(3), 151–156.

Ishii et al JP 07157439 Hcaplus Abstract #1995:773247, Jun. 1995.*

NGK –JP 59101145 WPI05 Abstract #84–180011(29), Jun. 1984.*

Mitsubishi –JP 60106459 HCaplus 1985:583602, Jun. 1985.*

Sugama et al: Chem. Conct. Res. 25(6) pp. 1305–1310 1995.*

Drenert: DE 4222763, Jan. 1994.*

Yoshiko et al JP 62–158485, Jul. 1987.*

Paul et al J. Mat. Sci. Lett. 14(24) pp. 1792–1794, 1995.*

* cited by examiner

HOLLOW BONE MINERAL-LIKE CALCIUM PHOSPHATE PARTICLES

GOVERNMENT RIGHTS

The United States government may have rights to certain aspects of this invention.

FIELD OF THE INVENTION

This invention relates to particles comprising silica-based, calcium and phosphate containing, glass compositions, and their transformation to calcium-phosphate shells in vitro.

BACKGROUND OF THE INVENTION

In U.S. Pat. No. 5,204,106, issued to Schepers et al., (hereby incorporated by reference) the implantation of bioactive glass granules having the composition: 45% SiO2, 24.5% $Na_2O$, 24.5% CaO and 6% $P_2O_5$, and a size range of 280–425 μm in diameter into the jaw of beagle dogs is disclosed. With particles of this size range, internal pouches formed in each of the particles and, subsequently, osteoprogenitor cells differentiated to osteoblasts within the pouches, actively laying down bone tissue. Next, bone tissue proliferated from the excavations, surrounded the particles and connected with bone tissue being formed around neighboring particles. Bone tissue was formed within the particle, without being bridged to the lingual or buccal bone plates. At 3 months, bone had grown throughout the surgical defects treated with glass granules. A similar phenomenon was not observed with particles of a larger size range, i.e., 480–800 micrometers, or a smaller size range, i.e., 210–300 micrometers.

Glass granules of narrow size range (300–360 μm) were used in a clinical trial in humans. Schepers et al., "Bioactive Glass Particles of Narrow Size Range: A New Material for the Repair of Bone Defects," *Implant Dentistry*, 2(3) :151–156, 1993, incorporated herein by reference. In this clinical study, 87 patients and 106 maxillo facial defects were treated. At 3 months, the application sites had fully solidified. At six months, no radiological difference between the defect sites and the surrounding bone could be discerned.

It was subsequently discovered that particles in the size range 200–300 micrometers effected the same results if implanted into sites exhibiting a reduced metabolic state, particularly as compared to the maxillo-facial sites. Such sites are found, for example, in the appendicular skeleton, and in certain disease states. U.S. application Ser. No. 08/268,510, hereby incorporated by reference.

The in vivo event which initiates the reactions leading to the formation of bone throughout the defects is an excavation of the particles. The excavation is the result of physicochemical reactions taking place in the glass, as well as a cell mediated resorption of the internal reaction layer. Bioactive glass reacts at its surface with the formation of two reaction layers: a silica gel below the surface and a calcium phosphate rich layer at the surface. In vivo, pouches of biologically formed calcium phosphate are formed. It is within these pouches that osteoprogenitor cells, which freely float around, undergo differentiation to cells expressing the osteoblastic phenotype. This differentiation does not occur outside these biologically formed calcium phosphate pouches.

Even so, it takes approximately one month for the particles to excavate in vivo. A means for further expediting the healing process would be advantageous.

SUMMARY OF THE INVENTION

The present invention can further expedite the healing process through the excavation of silica-based glass particles in vitro. According to the present invention, silica-based, Ca,P-containing glasses are transformed to hollow CaP-shells in vitro, prior to implantation. The silica-based glass granules can be melt- or sol-gel derived. The resultant hollow shells comprise an outer, nanoporous, carbonated amorphous or crystalline CaP-rich layer, with or without remaining silica.

In one aspect, the invention relates to the hollow particles which have been formed in vitro.

In another aspect, the invention relates to a method for producing the hollow calcium-phosphate particles according to the invention involving a differential immersion of the particles in solutions which provoke the dissolution of the silicon from the particles.

DETAILED DESCRIPTION

Hollow particles according to the present invention can be used to fill bony defects in sites present throughout the body of vertebrates for stimulating growth and repair. The hollow particles are formed as a result of in vitro excavation of silica-based, calcium and phosphate containing glass particles.

As used herein, "silica-based" refers to the inclusion of a silicon oxide in the composition of the glass. Other oxides may also be present.

The melt-derived silica-based, calcium and phosphate containing bioactive glass particles to be excavated according to the present invention can be prepared following, for example, the procedure disclosed in U.S. Pat. No. 5,204,106, hereby incorporated by reference. The composition for the melt-derived glass is as follows (in weight percent): $SiO_2$—40–60; $Na_2O$—10–32; CaO—10–32; and $P_2O_5$—0–12. Other compounds, and oxides, may also be present, such as described in P. Ducheyne, "Bioglass coatings and bioglass composites as implant materials," *J. Biomed. Mat. Res.*, 19:273–291, 1985, incorporated herein by reference.

The sol-gel derived particles can be prepared following, for example, the procedures disclosed in U.S. application Ser. No. 08/477,585, hereby incorporated by reference. The compositional range for the sol-gel derived glass is as follows (in weight percent): $SiO_2$—60–100; CaO—3–30; and $P_2O_5$—0–10.

The in vitro excavation of the silica-based, Ca,P-containing glass granules and transformation into CaP-shells is achieved by differential immersion of the glass granules in solutions which provoke the dissolution of silicon from the glass matrix. The differential immersion can be achieved by periodic solution exchange in a system in which the solution is static, or by use of a dynamic system in which the immersion solution is continuously supplied as a flow of fresh solution. See, U.S. Pat. No. 5,002,890, issued to Dennis R. Morrison on Mar. 26, 1991 for an example of how to achieve dynamic fluid replenishment in, that case, tissue culture.

The immersion conditions such as, for example, solution composition, duration, number of solution exchanges, material weight to solution volume ratio (W/V), can vary to a great degree. For example, without being limited thereto, the W/V can range from about 0.1 to about 5 mg/ml.

The solution conditions are selected to allow the following events to occur: 1) formation of a surface CaP layer; and 2) continuous dissolution of the silica-network, remaining under the CaP-layer, until about 80 to 100% of the original Si content in the glass is dissolved. In order to stimulate the continuous silica network dissolution, the solution used for the immersion must remain undersaturated with respect to soluble silica. Events 1) and 2) can be achieved by consecutively different solutions. For example, in the case of a glass composed of 100% silica, a calcium-phosphate surface layer must first be formed. This can be accomplished by immersing the glass in solutions saturated in silicon, such as described in U.S. application Ser. No. 08/647,007, filed concurrently herewith, hereby incorporated by reference.

The following reactions are involved in the transformation of the melt-derived glass granules: hydrolysis and formation of a silica-gel layer; migration of Ca and $PO_4$ ions from the bulk through the Si-gel to the surface; accumulation of the ions at the surface and formation of a CaP-rich surface; continuous growth of the Si-gel and CaP-rich layers; and continuous silica dissolution. When approximately 80 to 100% of the original Si-content is dissolved, the granules are transformed into voided CaP-shells.

The following reactions are involved in the transformation of sol-gel derived glass granules: loss of soluble silica along with migration of Ca and $PO_4$ ions through highly porous glass to the surface; leaching of the ions to a solution along with partial accumulation at the surface; formation of a CaP-surface layer; growth of the CaP-layer along with continuous silica dissolution.

Some solutions which can be used to achieve the glass excavation include, but are not limited to, the following:

a) water;
b) ion-free, tris buffer, with an initial pH of from about 6.8 to about 8.0—for melt-derived bioactive glass;
c) phosphate buffer solution with an initial pH of from about 6.8 to about 8.0; and
d) tris or phosphate buffer solutions containing varying concentrations of Ca and $PO_4$ ($HPO_4$ or $H_2PO_4$) with or without addition of varying concentrations of other ions including, but not limited, to Na, K, Cl, $CO_3$, and Mg, or their combination.

The only restriction is that the solution be undersaturated in silicon, i.e., solution saturation in silicon is never reached during the period of immersion. It is understood that, with increasing acidity, the absolute concentration of silicon at saturation decreases.

Because the hollowing out is achieved in vitro, the same constraints on particle size are not present as with in vivo excavations. Thus, glass particle size can vary to a large degree. In a preferred embodiment, the particles are from about 50 micrometers to about 5 millimeters—up to about 1 mm for melt-derived glass; and up to about 5 mm for sol-gel derived glass. With increasing particle size, the treatment duration and/or number of exchanges may also increase.

With increasing stability of the silica-based glass—such as increasing the amount of network former $SiO_2$, increasing the amount of network modifiers that render the network more stable (see Ducheyne, supra), or, in the case of melt-derived glass, replacing $Na_2O$ with a more stable alkali oxide—the duration of treatment and/or the number of solution exchanges will have to be increased, or the particle size will have to be reduced.

The dissolution of various forms of solid silica in aqueous solutions has been the focus of several studies. O'Connor et al., "The kinetics for the solution of silica in aqueous solutions," *J. Phys. Chem.*, 62:1195–8, 1958; and Iler, R. K., *The Chemistry of Silica: Solubility, Polymerization, Colloid and Surface Properties, and Biochemistry*, Wiley, N.Y., 1979. It has been established that any form of solid silica in contact with aqueous solutions dissolves into monosilicic acid $Si(OH)_4$ until the solution reaches saturation. By exchanging the immersion solution such that saturation is never reached, the diffusion process is favored and thus dissolution is enhanced. The in vitro dissolution behavior during the differential immersion is expected to be similar to that observed in vivo, during which the body fluid is continuously replenished.

During the differential immersion, the initial silicon content in the particles (either melt-derived or sol-gel derived) was completely released in solution, ultimately resulting in the formation of void Ca—P shells. A diffusion of silicon through the Ca—P layer is a possible explanation. We have found that this layer is highly porous.

The in vitro immersion to transform the silica-based glass granules to CaP shells can also be performed in solutions containing various biologically active molecules to produce shells coated with the biologically active molecules to enhance the process of healing and repair. Coating with the various biologically active molecules can be achieved during the immersion leading to the granule excavation and transformation into CaP-shells, or can follow the treatment for forming hollow particles as a separate stage. Alternatively, sol-gel derived bioactive glass particles can be prepared having the biologically active molecules incorporated in the matrix of the glass using the procedure as disclosed in U.S application Ser. No. 08/477,585, hereby incorporated by reference.

As used herein, the term "about" means approximately ±10%.

The term "bony defect", as used herein, refers to regions necessitating growth or repair including, but not limited to, fractures, areas of erosion and degradation, holes resulting from removal of screws and pins, replacements, periodontal applications, and deterioration of bone due to old age or disease.

As used herein, "biologically active molecules" are defined as those organic molecules having an effect in a biological system, whether such system is in vitro, in vivo, or in situ. Biologically active molecules include, but are not limited to, the following categories: growth factors, cytokines, antibiotics, anti-inflammatory agents, analgesics and other drugs, and cell attachment molecules.

The term "antibiotic" includes bactericidal, fungicidal, and infection-preventing drugs which are substantially water-soluble such as, for example, gentamicin, vancomycin, penicillin, and cephalosporins.

The term "growth factors" refers, without limitation, to factors affecting the function of cells such as osteogenic cells, fibroblasts, neural cells, endothelial cells, epithelial cells, keratinocytes, chondrocytes, myocytes, cells from joint ligaments, and cells from the nucleus pulposis. Platelet derived growth factors (PDGF), the transforming growth factors (TGF-β), insulin-like growth factors (IGFs), fibroblast growth factors (FGFs), and the bone morphogenetic proteins (BMPs) are examples of growth factors encompassed in the particles according to the present invention.

The term "cell attachment molecules" as used herein includes, but is not limited to, fibronectin, vitronectin, collagen type I, osteopontin, bone sialoprotein thrombospondin, and fibrinogen. Such molecules are important in the attachment of anchorage-dependent cells.

As is disclosed below, the presence of serum proteins in the immersion solution decreases the dissolution rate and, thus, increases the time for immersion and/or number of solution exchanges. A possible explanation is that the adsorption of the proteins on the surface of the glass modifies the surface of the glass in contact with solution.

In addition to their use for filling bone defects, the hollow particles according to the invention can also be used in microgravity tissue culture of anchorage-dependent cells. Some examples of anchorage-dependent cells include, but are not limited to, osteogenic cells, fibroblasts, neural cells, endothelial cells, epithelial cells, keratinocytes, chondrocytes, myocytes, cells from joint ligaments, and cells from the nucleus pulposis. For such cells, the conditions of attachment of the cells to a particular substrate greatly influences their subsequent function.

We have performed a preliminary analysis of the migration of a solid microcarrier in a Rotating-wall vessel (RWV). The following assumptions were introduced: 1) the equations of particle dynamics can be applied to the microcarrier's motion since the bead is infinitesimally small in size compared to surrounding medium; 2) physical properties of both liquid medium and solid particle are constants; 3) the flow field is not affected by the presence of the particle; 4) at time>0, the fluid is in solid body rotation equal to the angular velocity of the vessel—secondary flows can be neglected and the fluid flow is steady; and 5) the acceleration of the fluid due to the acceleration of the micrcocarrier is approximated by the virtual mass (M) concept, where , $m_b$ is the mass of microcarrier bead, and m is the mass of the displaced liquid.

The steady-state solution and its stability were determined for two conditions, when the microcarrier is less dense than the surrounding medium (m>$m_b$), and when the liquid medium is less dense than the bead (m<$m_b$). If m>$m_b$, the bead migrates toward an equilibrium position in the inertial frame or travels finally, after decay of the transient motion, on a concentric circle about the rotation axis in the rotating reference frame. If m<$m_b$, the particle moves away indefinitely. So, in order to maintain a stable system, our model suggests the use of a microcarrier that has an apparent density that is equal to or less than the surrounding medium. The "apparent density" is calculated by dividing the weight of the hollow particle by its volume.

Accordingly, particles which are to serve as carriers for cells in microgravity tissue culture vessels should have an apparent density of about 1.1 g/cm$^3$ or less. Hollow particles with an apparent density similar to this value can be made using the methods disclosed herein. Such particles possess a further advantage in that the Ca—P layer can serve as a substrate for fibronectin attachment. This molecule is an attachment molecule that serves as the ligand to the cell membrane, leading to cell attachment and, thus, prompting cellular activity. Thus, the particles can be prepared in a manner to incorporate cell attachment molecules in or on the calcium-phosphate shell. Accordingly, use of the particles according to the invention in microgravity culture is not restricted to bone tissue cells, but is universally applicable to anchorage-dependent cells in general including, but not limited to, fibroblasts, neural cells, endothelial, epithelial cells, keratinocytes, chondrocytes, myocytes, hepatocytes, cells from joint ligaments, and cells from the nucleus pulposis.

EXAMPLE 1

Preparation of Sol-Gels

Three types of sol-gel derived particles were synthesized: 100% silica (S100), Vancomycin-silica composites (S100V), and calcium and phosphorus containing silica (S70).

S100V contained 1.2 mg of Vancomycin per gram. S70 was composed of: 70% $SiO_2$, 25% CaO and 5% $P_2O_5$ (% by weight)

The alkoxides tetramethyl orthosilicate (TMOS—Aldrich Chemical Inc., Milwaukee Wis.), calcium methoxyethoxide (CME—Gelest Inc.,Tullytown Pa.) and triethyl phosphate (TEP— Strem Chemical Inc., Newburyport Me.) were used as silicon, calcium and phosphorus sources respectively.

S100 and S100V were prepared from a mixture of TMOS and deionized (DI) water in a 1:10 molar ratio. The following procedure was used. Predetermined amounts of TMOS and deionized water, to maintain the molar ratio for the volume prepared, were poured into a beaker which was immediately placed in an ice-cooled ultrasonic bath. For the Vancomycin-containing sol-gel, the amount of water added at this point precludes the amount of water to be added later with the antibiotic. Sonification was performed in the absence of solvent to prevent phase separation. Since sonification provides energy, ice cooling was used to prevent overheating. A small volume of acid catalyst (1N HCl) was then added. Within a few minutes, the mixture became homogenous. Ultrasonic stirring was continued for 20 to 25 minutes and the pH of the solution was measured. The pH did not exceed 3. While the sol was still being stirred and cooled, a previously prepared solution of Vancomycin (Vancoled—Lederle Parentals Inc., Carolina and Puerto Rico) in DI water was added when necessary. The solution was stirred for another five minutes. The sols were cast into preweighed polystyrene vials using a volumetric pipette. Three milliliters were dispensed into each vial. Next, the vials were weighed, sealed, and set aside to allow gelation to occur. The time to gelation was approximately 15 hours.

The gels were left to age for 3 days, with the vials remaining sealed. Afterwards, the gels were exposed to ambient air and dried to 70% loss of the as-cast weight. The disks obtained were then crushed with a ceramic mortar and pestle, and sieved in a sonic sifter to produce particles of two diameter ranges: 210–500 micrometers and 500–710 micrometers. The resulting particles were stored in sealed polystyrene containers at 4 C.

The calcium and phosphorus containing sol was prepared in a glove box under an argon atmosphere. The following procedure was used. Prorated amounts of TMOS, CME, and TEP to arrive at s sol-gel composition having a final composition of 70% $SiO_2$, 25% Cao and 5% $P_2O_5$ (% by weight), were successively poured in a beaker. The mixture was magnetically stirred for about 5 minutes. The sol was cast into preweighed polystyrene vials, 2.23 ml per vial. After casting, the samples were removed from the glove box. To delay gelation, methanol was added in a 1:1 molar ratio with TMOS. The samples were vortexed immediately thereafter. Next, 0.1 N acetic acid was added to each sample to simulate the addition of biologically active molecules dissolved in an acidic solution. Gelation occurred within a minute. The remainder of the procedure was the same as for the silica sol-gels.

The particles were characterized by gas sorption (Quantachrome Autosorbl) and Fourier Transform Infrared Spectroscopy (FTIR, Nicolet 5DXC). The gas sorption analysis indicated that the materials were highly porous. The FTIR spectra revealed absorption bands typical of a silica network.

EXAMPLE 2

Immersion Experiments

The specimens prepared according to Example 1 above were immersed in three solutions: TE, TE supplemented with 10% serum (vol %), and 100% serum. The solutions were chosen to address effect of important constituents of the in vivo milieu. Immersions were performed invials. TE is a non-proteinaceous control that contains the electrolyte constituents of human blood plasma in similar concentrations (cf. Table I). TE was prepared by dissolving reagent grade NaCl, KCl, NaHCO$_3$, MgCl$_2$.6H$_2$O, MgSO$_4$.7H$_2$O, KHPO$_4$anh. and CaCl$_2$.2H$_2$O in a 0.05 M Tris [hydroxymethyl] aminomethane hydrochloride buffered solution. The resulting pH was 7.4 at 37° C. New-born calf serum was used to study the possible effects of serum proteins on the in vitro behavior of the materials.

TABLE I

Ionic content of human blood plasma and TE.

| Ion | Human blood plasma (mM) | TE (mM) |
|---|---|---|
| Ca$^{2+}$ | 2.5 | 2.5 |
| HPO$_4^{2-}$ | 1.0 | 1.0 |
| Na$^+$ | 142.0 | 152.0 |
| Cl$^-$ | 103.0 | 136.0 |
| K$^+$ | 5.0 | 5.0 |
| Mg$^{2+}$ | 1.5 | 1.5 |
| HCO$_3^-$ | 27.0 | 27.0 |
| SO$_4^{2-}$ | 0.5 | 0.5 |

A differential immersion was effected by exchange with fresh solution at various time points throughout the duration of immersion. In the present example, the samples were exposed to fresh solution after 3, 6, 9, 24, 48, 72, 96, 124 and 168 hours of immersion. These intervals were chosen in an attempt to maintain a maximum concentration of Si in solution less than ⅔ of the saturation concentration. The immersion protocol was intended to reflect the continuous replenishment of body fluid at the implant site. The samples were immersed for up to 7 days.

Three samples were tested per set of conditions. The weight to solution volume ratio was 0.5 mg/ml. The samples were placed in an incubator at 37° C. in a 5% CO$_2$ atmosphere and continuously shaken (200 revolutions/minute). The vials were loosely capped to minimize evaporation without preventing gas exchange.

The testing conditions (i.e.,sample, immersion mode, and solution) and the parameters studied are listed in Table II. Upon completion of the selected immersion protocols, the solutions were collected and the retrieved particles were rinsed with ethanol and dried in ambient air.

TABLE II

| | Testing conditions | |
|---|---|---|
| Composition | Particle size | Solution |
| S100 | 500–710 μm | TE |
| S100V | | |
| S70 | | |
| S70 | 210–500 μm | TE |
| S70 | 500–710 μm | TE |
| | | TE + 10% serum |
| | | serum |

The Si and Ca concentrations were measured by flame atomic absorption spectrophotometry (FAAS, Perkin-Elmer 5100PC). The P concentration was determined using a calorimetric method (Heinoken et al., "A new and convenient calorimetric determination of inorganic orthophosphate and its application to the assay of inorganic pyrophosphate," *Anal. Biochemistry*, 113:313–7, 1981,) (Molybdenum yellow) (Pharmacia LKB Ultrospec Plus Spectrophotometer).

Figure 2A:
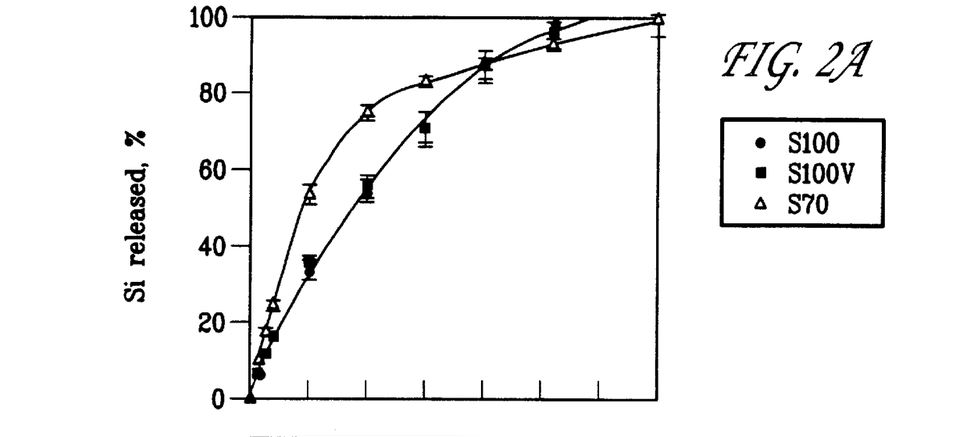
FIGS. 2a–c depict the changes in Si, Ca, and P content, respectively, during immersion of sol-gel derived particles as a function of glass composition.
Figure 2B:
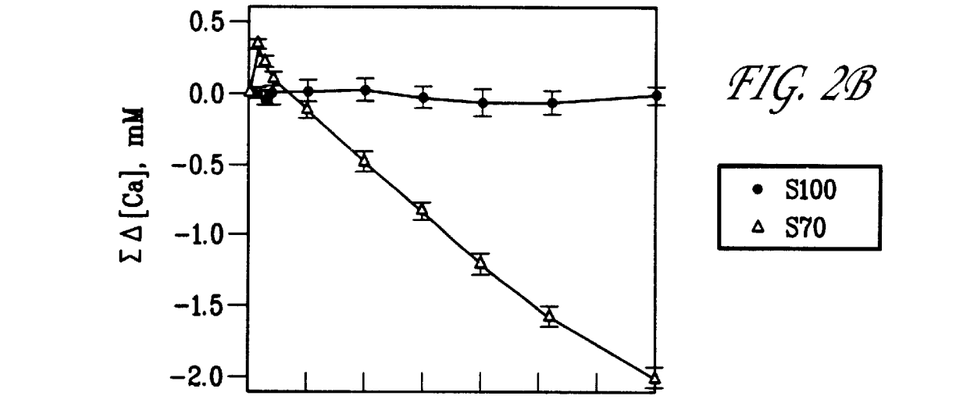
Figure 2C:
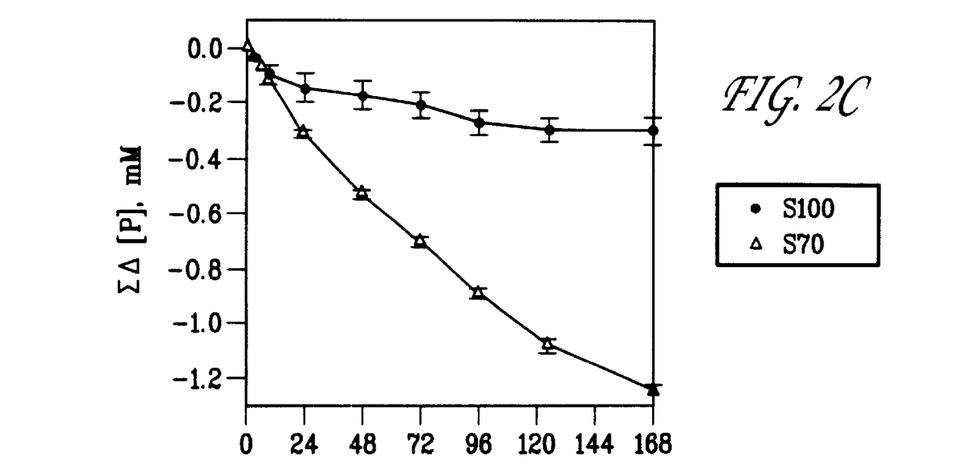

The cumulative variation of the Si, Ca, and P concentration in TE as a function of time of immersion is shown in FIGS. 2a–c. The error bars represent the standard deviation of the means. As is evident from FIG. 2a, 800 of the initial silicon content is released from the S70 glass after 48 hours of immersion and no silicon remained after a 7-day period. FIGS. 2b and 2c show that the Si dissolution from S70 is accompanied by the formation of a Ca—P phase, as indicated by a continuous calcium and phosphate uptake from solution. For S100 glass, 60% of the initial silicon was released after 72 hours and, again, no silicon remained after a 7-day period. However, Si dissolution from S100 was not accompanied by a formation of a Ca—P phase, as indicated by the lack of uptake of calcium and phosphate from solution. The presence of Vancomycin in S100 did not affect the dissolution behavior of the composite, as indicated by the similar release profiles.

To determine the immersion-induced compositional and structural changes, the reacted particles were analyzed with the same techniques as used for the characterization. In addition, scanning electron microscopy in combination with energy dispersive x-ray analysis (SEM-EDXA, JEOL T300A) was employed.

FTIR analysis confirmed the formation of a calcium-phosphate material with the characteristics of a crystalline, carbonated hydroxyapatite similar to bone-mineral calcium phosphate.

Figure 3:
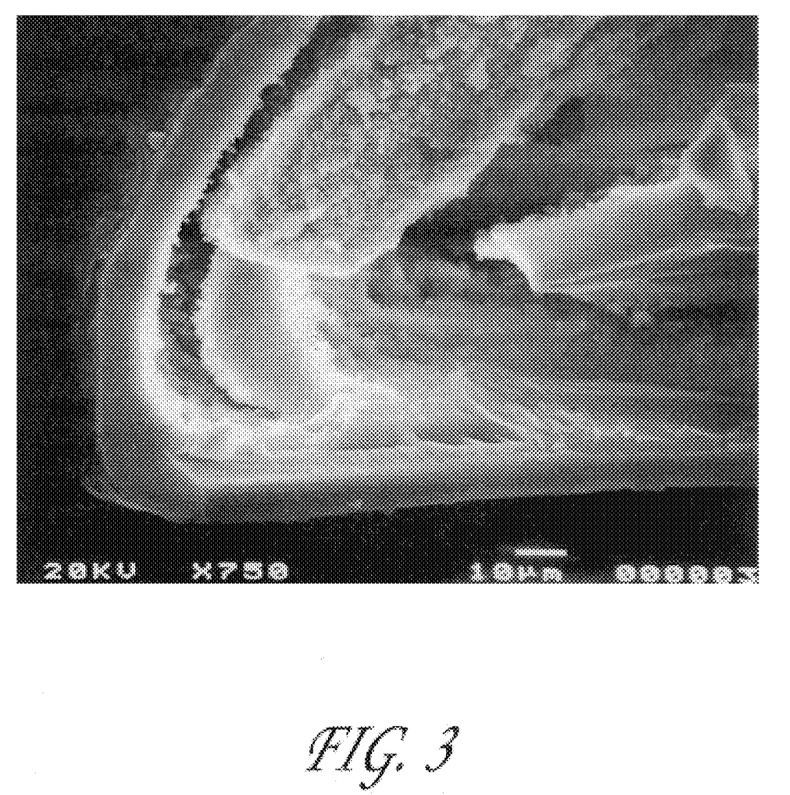
FIG. 3 is a Scanning Electron Micrograph depicting a hollow calcium-phosphate particle according to the invention formed from sol-gel derived glass.

SEM micrographs of S70 reacted particles show that the particles are transformed into Ca and P containing shells (see FIG. 3, X 750). The sample was prepared for SEM examination by fracturing it. As a result, the interior of the particle was exposed. The SEM examination revealed that the particle had been transformed into a shell by the immersion treatment.

EDXA analysis only detected calcium and phosphorus, but no silicon. The Ca/P ratio of the shell as measured by EDXA is 1.5. The shell was approximately 10 μm thick.

Figure 4:
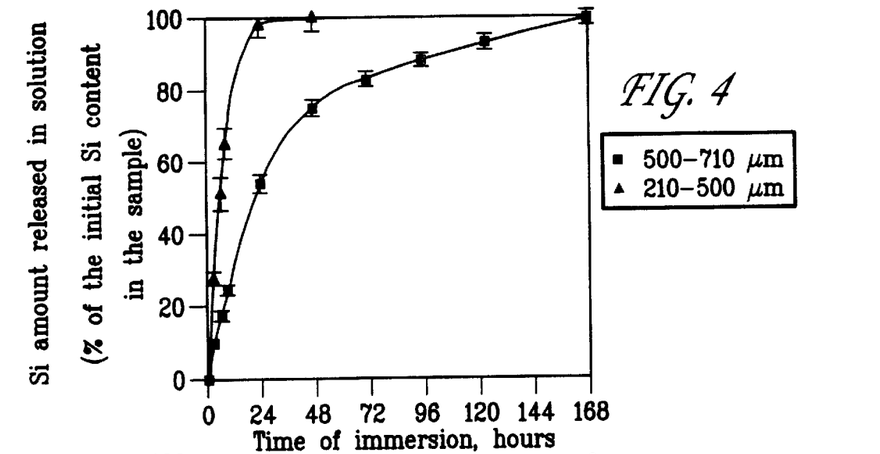
FIG. 4 depicts changes in Si content during immersion of sol-gel derived particles of S70 glass composition as a function of particle size.

FIG. 4 shows the silicon release profile S70 particles of two sizes ranges. These results indicate that the dissolution rate increases with decreasing particle size or increasing external surface area. Moreover, the S70 particles of the smaller size range exhibit the same transformation into shell-like shape as found for the larger particles.

Figure 5:
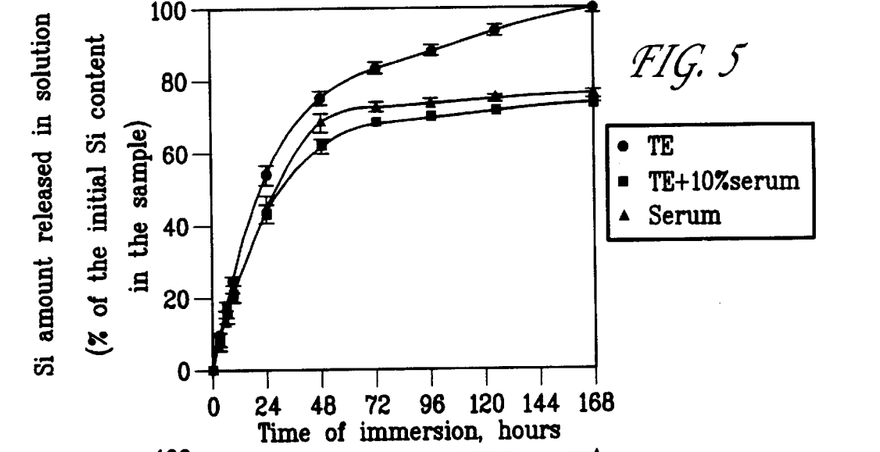
FIG. 5 depicts the effect of serum proteins on amount of Si released for S70 sol-gel derived glass particles.

FIG. 5 shows the dissolution behavior of S70 in TE, TE supplemented with 10% serum, and serum. The presence of serum in the immersion solution decreased the rate of dissolution. Statistical analysis revealed that the release profiles differed significantly among solutions ($p<0.05$, analysis of variance) except for TE supplemented with 110% serum and 100% serum.

EXAMPLE 3

Transformation of Melt-derived Glass 45S5 Granules Into Hollow Ca,P-shells

Granules, 200–300 $\mu$m, of melt-derived glass 45S5 (W,%:45 $SIO_2$, 25.5 $Na_2O$, 24.4 CaO, and $P_2O_5$), prepared according to the procedure disclosed in U.S. pat. No. 5,204,106, were immersed in tris buffered (pH 7.4 at 37° C.) physiological solution with electrolyte content similar to that of the plasma (TE) at a weight/solution volume ratio of 0.5 mg/ml and tested in triplicate in a differential mode at 37° C. The solutions were exchanged at 3, 10, 24, 48, 72, 96, 120, and 144 hours. The total time of immersion was 168 hours.

The concentrations of Si, dissolved from the glass granules, were measured in the post-immersion solutions using flame atomic absorption spectroscopy (Perkin-Elmer, 5100). The post-immersion materials were analyzed using scanning electronmicroscopy (SEM) combined with energy-dispersive X-ray analysis (EDXA). Some of the post-immersion particles were punched with a needle under an optical microscope to expose the inner surfaces.

Figure 1:
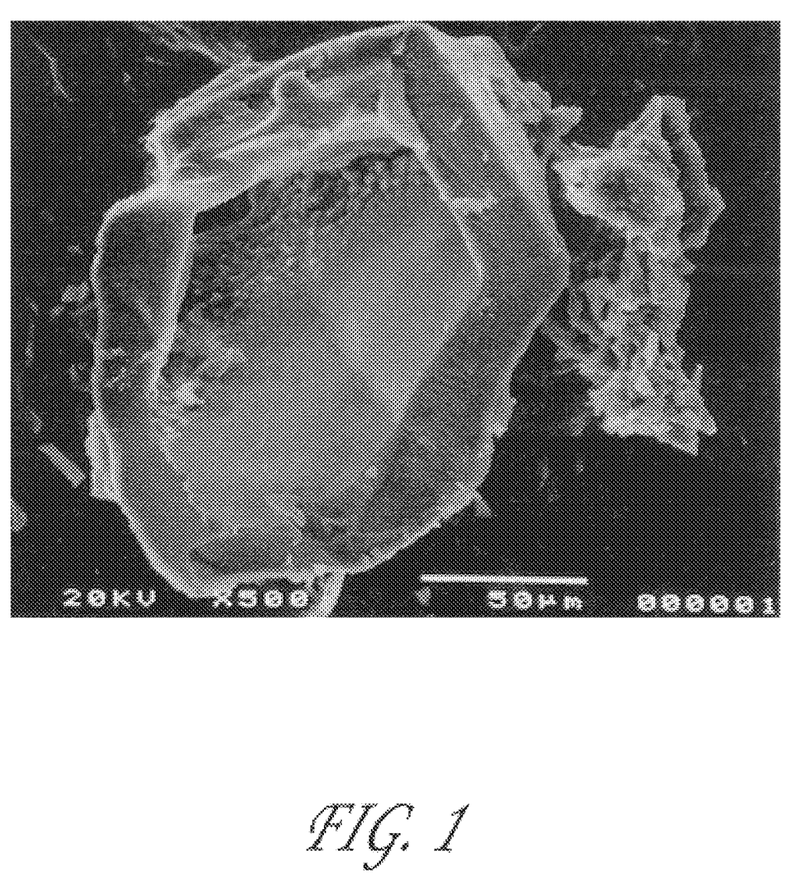
FIG. 1 is a Scanning Electron Micrograph depicting a hollow calcium-phosphate particle according to the invention prepared from melt-derived 45S5 glass.
Figure 6:
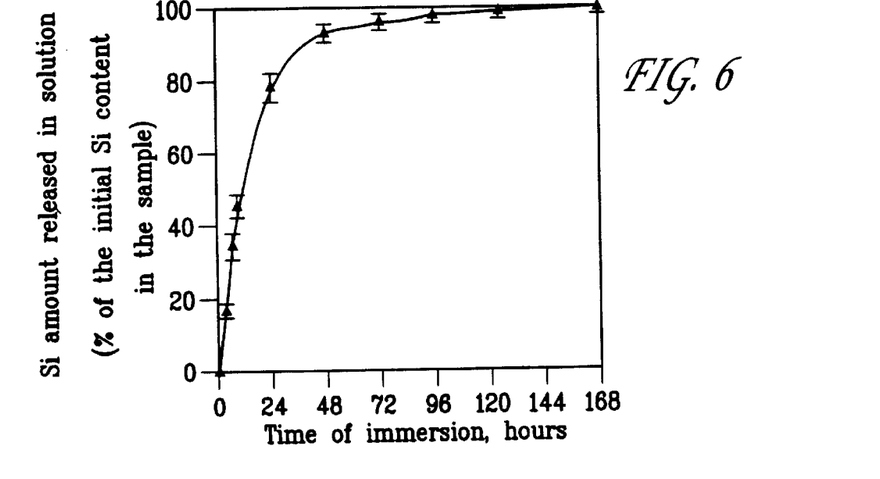
FIG. 6 depicts changes in Si content during immersion of melt-derived particles.

FIG. 6 shows the percentage of Si dissolved from the glass, versus the immersion time. FIG. 1 shows the SEM image of the interior surface of a post-immersion particle.

The data, presented in FIG. 6, indicate that 80% of the initial Si content in the 45S5 glass was dissolved after 24 hours of the differential immersion (which included 4 solution exchanges by this time), and all the Si content was dissolved by 168 hours.

The SEM photograph shows a hollow particle with a shell about 10 $\mu$m thick. Both the outer layer and the inner surface of the shell comprised a Ca,P-phase as was indicated by EDXA. No remaining Si was detected inside the post-immersion particle.

Thus, the data obtained demonstrate a total transformation of the starting 45S5 glass granules (200–300 $\mu$m) into hollow Ca,P-shells during the differential immersion in TE.

The foregoing examples are meant to illustrate the invention and not to limit it in any way. Those skilled in the art will recognize that modifications can be made which are within the spirit and scope of the invention as set forth in the appended claims.

What is claimed is:

1. A hollow particle having an intact nanoporous calcium phosphate shell, said nanoporous calcium phosphate shell further comprising up to about 9.3% silicon, and having an outer diameter of up to about 5 mm, said hollow particle prepared by the process comprising the step of immersing bioactive glass particles comprising from about 40% to about 100% SiO, in an aqueous solution undersaturated in soluble silica for a period sufficient to allow from about 80% to about 100% of the silicon to dissolve from said bioactive glass particles.

2. The hollow particle of claim 1, wherein said hollow particle further comprises biologically active molecules.

3. The hollow particle of claim 2 wherein said biologically active molecules comprise an antibiotic.

4. The hollow particle of claim 3 wherein said antibiotic is vancomycin.

5. The hollow particle of claim 2 wherein said biologically active molecules comprise cell attachment molecules.

6. The hollow particle of claim 2 wherein said biologically active molecules comprise growth factors.

7. The hollow particle of claim 1, said hollow particle having an apparent density of about 1.1 $g/cm^3$.

* * * * *